United States Patent [19]

Motitschke et al.

[11] Patent Number: 5,006,337

[45] Date of Patent: Apr. 9, 1991

[54] MEDICINAL COMPOSITIONS BASED ON SPENT BREWERS' GRAINS EXTRACT, A PROCESS FOR THE PREPARATION THEREOF, AND THE USE OF SPENT BREWERS' GRAINS EXTRACT FOR THE PREPARATION OF COSMETIC COMPOSITIONS, AND A SPECIAL BREWERS' GRAINS EXTRACT

[75] Inventors: Lothar Motitschke, Hilden; Hagen Tronnier, Dortmund, both of Fed. Rep. of Germany

[73] Assignee: Marbert GmbH, Dusseldorf-Holthausen, Fed. Rep. of Germany

[21] Appl. No.: 181,408

[22] Filed: Apr. 14, 1988

[30] Foreign Application Priority Data

Apr. 16, 1987 [DE] Fed. Rep. of Germany ....... 3712986

[51] Int. Cl.$^5$ .................. A61K 35/78; A61K 7/06
[52] U.S. Cl. .................. 424/195.1; 424/74; 514/829; 514/844; 514/858; 514/859; 514/861; 514/862; 514/863; 514/864; 514/865; 514/880; 514/886; 514/887
[58] Field of Search .............. 424/195.1, 74; 514/858, 514/859, 860, 861, 862, 863, 864, 865, 880, 881, 886, 887, 817, 829, 844, 845, 846, 847, 848

[56] References Cited

U.S. PATENT DOCUMENTS 3,998,761  12/1976  Gary et al. .................. 424/70 X
4,634,588   1/1987  Moroe .......................... 424/49 X

FOREIGN PATENT DOCUMENTS 7703375  9/1978  France .

OTHER PUBLICATIONS

The Merck Manual, Fifteenth Edition, pp. 2254–2263, 1987.
"Parfums, Cosmetiques, Aromes", No. 55, Feb.–Mar. 1984, pp. 47–54.
C.A., vol. 96, No. 205224e, 1982.
SU 1,242,190, 3/1987.
European Search Report.

*Primary Examiner*—John W. Rollins
*Attorney, Agent, or Firm*—Finnegan, Henderson, Farabow, Garrett and Dunner

[57] ABSTRACT

Medicinal and cosmetic compositions for the treatment of skin disorders and for care of dry and/or irritated skin and of dry scalp with dandruff are prepared using brewers' grains extract(s)—especially a brewers' grains extract obtained using liquid or above-critical $CO_2$ or $N_2O$.

11 Claims, No Drawings

MEDICINAL COMPOSITIONS BASED ON SPENT BREWERS' GRAINS EXTRACT, A PROCESS FOR THE PREPARATION THEREOF, AND THE USE OF SPENT BREWERS' GRAINS EXTRACT FOR THE PREPARATION OF COSMETIC COMPOSITIONS, AND A SPECIAL BREWERS' GRAINS EXTRACT

Medicinal compositions based on brewers' grains extract, a process for the preparation thereof, and the use of brewers' grains extract for the preparation of cosmetic compositions, and a special brewers' grains extract.

The mash remaining ("sludge") in the brewing of beer after the addition of hops was formerly used to prepare medicinal and cosmetic baths which were regarded as a type of "fountain of youth"; the effect of these bath essences is attributed to the estrogens originating from the hops (Seifen-Öle-Fette-Wachse No. 17/1961, page 530 and No. 18/1961, page 555).

It is said that deodorant cosmetic products are obtainable from another byproduct of the brewing of beer, the spent brewers' grains which are produced before the addition of hops (French Patent No. 77,03,375, Publication No. 2,379,282). For this purpose, the brewers' grains are extracted with a suitable solvent—the French patent mentions alcohols (methanol, ethanol, butanol, isopropanol), ethers, ketones and water (where appropriate with additions of acids or bases)—and the extract is concentrated and solids are filtered off where appropriate, or else solvent is completely removed. The relevant cosmetic products (lotions, creams, gels, sprays etc.) are then prepared in a customary manner from the extract which has been concentrated or from which solvent has been completely removed.

As has been shown by reproduction, the spent grains extracts obtained as stated in the abovementioned French patent are all rather dark (brown) in color, which is a disadvantage for the preparation of cosmetic products which are white or pale in color. Furthermore, although these extracts have the property of eliminating, or at least reducing, sweat and unpleasant body odors, on the other hand they themselves have a characteristic odor which, in some cases, is rather unpleasant (pungent). The composition stated in the French patent as the composition determined by chromatography on the extract from which solvent has been removed is the following:

Constituents of an ethanolic extract:
hordenine (4-(2-dimethylaminoethyl)phenol)
amino acids (alanine, asparagine, glutamine, glutamic acid, isoleucine, methionine, phenylalanine, proline, serine, threonine, tyrosine, valine)
fatty acids (α-aminobutyric acid, citric acid)
sugars (fructose, glucose, sucrose, raffinose)
electrolytes.

The starting material for the preparation of the cosmetic products—what is called the spent brewers' grains—is, according to M. Becker and K. Nehring (Handbuch der Futtermittel (Animal Feed Handbook) 3, p. 102, published by P. Parey, Hamburg, Berlin, 1967), obtained as follows:

It is possible to use various types of cereals as starting materials; certain types of barley are preferably employed. The cereals are preferably initially steeped in water for a few days to initiate the germination process. Subsequently, at a temperature of, preferably, about 17°–18° C., the germination of the cereal grains takes place, with the formation of enzymes, essentially α- and β-amylases which are necessary for the conversion of the carbohydrates into fermentable sugars. After several days, the germination process is terminated by cautious heating and drying of the grains. The malt which is thus produced is milled in the next operation, a defined amount of water is added, and the mixture is heated to a temperature of, preferably, about 70°–75° C., which initiates the saccharification process. The insolubles removed from the suspension after saccharification is complete are called spent grains and are produced in large amounts in the brewing of beer. Details of the composition and analysis of spent brewers' grains are to be found in the table which follows and is from "Mit Biertrebern mehr Ertrag und mehr Gewinn" (Higher yields and more profits with spent brewers' grains) (information brochure from Tremonis GmbH, Westfälische Str. 251, 4600 Dortmund 12).

Composition of spent brewers' grains

|  |  | Fresh from to | Ensiled from to |
|---|---|---|---|
| Dry matter DM (in %) |  | 21.8–24.7 | 23.6–27.1 |
| Nutrients (in % of DM) | Crude protein | 22.5–27.5 | 22.3–26.3 |
|  | Crude fat | 5.5–9.5 | 6.6–10.8 |
|  | Crude fiber | 16.2–21.2 | 17.6–22.4 |
|  | Crude ash | 3.8–6.2 | 3.7–6.7 |
|  | N-free extractives | 40.0–47.0 | 37.3–45.7 |
|  | Starch |  | 7.9–9.2 |
|  | Sugars |  | 1.3–1.6 |
| Minerals (in % of DM) | Calcium | 0.27–0.49 | 0.20–0.46 |
|  | Phosphorus | 0.57–0.77 | 0.43–0.73 |
|  | Sodium | 0.10–0.90 | 0.23–0.45 |
|  | Magnesium | 0.17–0.27 | 0.10–0.34 |

| Trace elements (in mg per kg DM) | Iron | 190 | Manganese | 50 | Cobalt | 0.18 |
|---|---|---|---|---|---|---|
|  | Zinc | 85 | Copper | 14 | Selenium | 0.10 |
| Amino acids (in % of DM) | Lysine | 1.1 | Glutamic acid | 4.3 | Leucine | 1.6 |
|  | Methionine | 0.6 | Proline | 2.0 | Tyrosine | 0.7 |
|  | Cystine | 0.5 | Glycine | 0.9 | Phenylalanine | 0.1 |
|  | Aspartic acid | 1.4 | Alanine | 1.0 | Histidine | 0.5 |
|  | Threonine | 0.9 | Valine | 1.3 | Arginine | 1.2 |
|  | Serine | 0.8 | Isoleucine | 0.9 | Tryptophan | 0.2 |

| Vitamins (per kg DM) | Vitamin $B_1$ 1.26 mg | Vitamin $B_{12}$ 38.90 mcg | Ca d-pant. 3.03 mg |
|---|---|---|---|
|  | Vitamin $B_2$ 0.91 mg | Folic acid 0.07 mg | Biotin 140.00 mcg |
|  | Vitamin $B_6$ 0.62 mg | Nicotinic 38.90 mg | Vitamin E 25.70 mg |

-continued

| | | acid | | | | |
|---|---|---|---|---|---|---|
| Fatty acids | C 8:0 | 0.1 | 16:0 (palmitic) | 21.7 | 20:0 | 0.8 |
| (in % of the fat) | 10:0 | — | 18:0 (stearic) | 5.0 | 22:0 | 2.9 |
| | 12:0 | 0.5 | 18:1 (oleic) | 13.3 | 22:1 | 3.0 |
| | 14:0 | 1.3 | 18:2 (linoleic) | 27.5 | 24:0 | 1.3 |
| | | | 18:3 (linolenic) | 10.8 | remainder | 11.8 |

It has now been found that the spent grains' extracts obtained as described above also have a curative effect on certain skin disorders associated, in particular, with pruritus and inflammatory manifestations, and are also suitable for the preparation of cosmetic products for care of dry and/or irritated skin and of dry scalp with dandruff.

Particularly advantageous spent grains' extracts for this purpose are those extracts obtained by extraction of spent brewers' grains with liquid or above-critical $CO_2$ or $N_2O$—and having only a pale color (golden yellow) and a pleasant odor of cereals. This is extremely surprising because it was to be assumed, on the basis of the abovementioned citation in the journal Seifen-Öle-Fette-Wachse, that the only waste or byproducts from the brewing of beer to have a curative effect are those containing the estrogen originating from the hops; however, spent grains obtained before the addition of hops contain no estrogens, as is evident from the abovementioned composition analysis. It is unambiguously clear from the extract composition stated in the French patent that estrogens of this type are not formed during the extraction procedure either.

Furthermore, on the basis of the deodorant effect, mentioned in the French patent, of the relevant spent brewers' grains extracts, it was not possible in any way to expect the suitability, which is entirely different in type, for the treatment and care of skin which tends to dryness and/or is irritated and of dry scalp with dandruff, because deodorant products are normally applied in regions of body where sweating is pronounced (armpits etc.)—that is to say on moist skin.

Hence the invention relates to a medicinal composition which contains or is composed of spent brewers' grains extract. The spent brewers' grains extract can be prepared using any desired cereals (for example barley, wheat, oats, rice, corn); however, certain types of barley are to be preferred, such as, for example, Hordeum distichum, Hordeum tetrastichum or Hordeum hexastichum, especially Hordeum distichum. The spent brewers' grains can be extracted wet or dry, preferably dry. Suitable in principle as extractants are all the extractants listed in the abovementioned French patent, such as alcohols, ethers, ketones, water, where appropriate with addition of acidic or basic substances. Also suitable are, furthermore, other solvents such as, for example, hydrocarbons (for example petroleum ether, hexane, toluene), lower halogenated aliphatic hydrocarbons (for example dichloromethane, trichlorofluoromethane etc.), esters (for example ethyl formate, methyl acetate, ethyl acetate etc.) and, preferably, both $CO_2$ and $N_2O$ in the liquid or above-critical range; the particularly preferred solvent is $CO_2$ in the above-critical range.

Extraction with the conventional solvents (which are liquid under normal conditions) is carried out in a manner which is customary per se, as is described, for example, in the French patent. Extraction using liquid or above-critical $CO_2$ is likewise carried out in the customary way, and described, for example, in "Carbon dioxide extracted ingredients for fragrances" (information brochure from Pauls Flavours & Fragrances 0-5M385P, North Albert Road, Reigate, Surrey RH2 9ER, UK) or "Hochdruck-Extraction" (High-pressure extraction) (Information Brochure Hi 5 19200085 - HT80-5d+e+f Uhde GmbH, Buschmühlenstr. 20, 5800 Hagen 1); preferred parameters for the extraction of spent grains with above-critical $CO_2$ are pressures of about 75 to 600 bar, in particular between about 150 and 350 bar, and temperatures of about 31° to 120° C., preferably of about 40° to 90° C.; preferred parameters for the extraction of spent grains with liquid $CO_2$ are pressures between about 50 and 250 bar, in particular about 100 to 150 bar, and temperatures between about −10° and 31° C., in particular between about 10° and 20° C.

Extraction with liquid or above-critical $N_2O$ is carried out in virtually the same way and under the same conditions, merely the preferred temperature limit for working with liquid and above-critical $N_2O$ being slightly higher—namely at about 36.5° C.—than on extraction with $CO_2$ (about 31° C.).

The extracts obtained using conventional liquid solvents have to be concentrated or evaporated. The extracts obtained with liquid or above-critical $CO_2$ or $N_2O$ are, by their nature, almost completely free of extractant under normal conditions. Analysis by thin-layer chromatography shows that the compositions of the individual extracts hardly differ from one another. However, whereas the extracts obtained using conventional liquid solvents are dark in color and some of them have a pungent odor, the $CO_2$— and $N_2O$-extracts have a golden yellow color and a pleasant odor resembling cereals. The drop point of the $CO_2$ extracts is between about 35° and 39° C.

The compositions according to the invention are suitable as agents for skin disorders, preferably for skin disorders associated with pruritus and/or inflammatory manifestations, especially for atopic dermatitis, ichthyosis, preeczematous states, pruritus, sebostasis and mycoses of the skin, and skin irritations resulting from jellyfish stings. Because of the absence of a vasoconstrictor effect, the mechanisms of action must differ from those of antihistamines and corticosteroids. Since antihistamines often have only slight local efficacy, and corticosteroids have the known side effects, the compositions according to the invention represent a therapeutic alternative.

The medicinal products based on the spent brewers' grains extracts are preferably intended for external use. Examples of application forms which may be mentioned are solutions, suspensions, emulsions, pastes, ointments, gels, creams, lotions, dusting powders, soaps, surfactant-containing cleansing products, oils and sprays. Any desired customary excipients, auxiliaries and, where appropriate, further active substances are added to the composition, in addition to the spent brewers' grains extract. Auxiliaries which are to be preferred are derived from the group of preservatives, antioxidants, stabilizers, solubilizers, vitamins, colorants and odor improvers.

Ointments, pastes, creams and gels can, besides the active substance(s), contain the customary excipients, for example animal and vegetable fats, waxes, paraffins, starch, tragacanth, cellulose derivatives, polyethylene glycols, silicones, bentonite, silica, talc and zinc oxide, or mixtures of these substances.

Dusting powders and sprays can, besides the active substance(s), contain the customary excipients, for example lactose, talc, silica, aluminum hydroxide, calcium silicate and polyamide powder, or mixtures of these substances. Sprays can additionally contain the customary propellants, for example chlorofluorohydrocarbons, propane/butane or dimethyl ether.

Solutions and emulsions can, besides the active substance(s), contain the customary excipients such as solvents, solubiizers and emulsifiers, for example water, ethanol, isopropanol, ethyl carbonate, ethyl acetate, benzyl alcohol, benzyl benzoate, propylene glycol, 1,3-butylglycol, oils, especially cottonseed oil, peanut oil, corn oil, olive oil, castor oil and sesame oil, glycerol fatty acid esters, polyethylene glycols and fatty acid esters of sorbitan, or mixtures of these substances.

Suspensions can, besides the active substance(s), contain the customary excipients such as liquid diluents, for example water, ethanol or propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

Soaps can, besides the active substance(s), contain the customary excipients such as, for example, alkali metal salts of fatty acids, salts of fatty acid hemiesters, fatty acid protein hydrolyzates, isethionates, lanolin, fatty alcohols, vegetable oils, plant extracts, glycerol, sugars, or mixtures of these substances.

Surfactant-containing cleansing products can, besides the active substance(s), contain the customary excipients such as, for example, salts of fatty alcohol sulfates, fatty alcohol ether sulfates, sulfosuccinic hemiesters, fatty acid protein hydrolyzates, isethionates, imidazolinium derivatives, methyllaurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Oils for the face or body can, besides the active substance(s), contain the customary excipients such as, for example, synthetic oils such as fatty acid esters, fatty alcohols, silicone oils, natural oils such as vegetable oils, and oily plant extracts, liquid paraffins, lanolin oil, or mixtures of these substances.

The concentration of the spent brewers' grains extract in the medicinal compositions according to the invention is between 0.5 and 100% by weight, preferably between about 5 and 99% by weight. The medicinal composition is prepared by converting, in a manner customary per se, the spent brewers' grains extract and the particular additives into the particular administration form which is desired.

The invention also relates to the use of spent brewers' grains extracts for the preparation of cosmetic compositions for care of dry and/or irritated skin and of dry scalp with dandruff. Since it is particularly important for a cosmetic product to have a pleasant odor and an attractive color, the $CO_2$— and $N_2O$-extract of spent brewers' grains is particularly valuable in this connection. Because of its only slight color and its pleasant characteristic odor, it can be used in higher concentrations than the conventional extract without having a disagreeable effect.

The application forms of the cosmetic products are, in principle, the same as for the medicinal compositions and, furthermore, also embrace typical cosmetic application forms such as lipsticks, sticks for lip care, mascara, eye liners, rouge, powder and emulsion makeups etc., as well as sunscreen and after-sun products. The ingredients of cosmetic compositions are essentially the same as for the medicinal compositions. The proportion of spent brewers' grains extract is preferably between about 0.1 and 99% by weight, in particular between about 1 and 10% by weight.

I. INVESTIGATION OF THE THERAPEUTIC EFFICACY

Test A: Histamine Wheal Test

The test was carried out as follows:

Defined amounts of the test products were applied to the predetermined areas measured on the skin of the back with a diameter of 7 cm. After an exposure time of 15 minutes, the inuncted areas were covered with a fabric and, after an exposure time of 2 hours, histamine wheals were produced in the centers of the fields using 0.02 ml of a 1/1000% strength histamine solution.

After 10, 20, 30, 40, 60 and 90 minutes, the areas of erythema and the sizes of the wheals in the measured areas were determined by planimetry. The number of subjects for this test was 10. It emerged that all the tested products brought about a distinct diminution in the reactions compared with the control field, which demonstrates the antiinflammatory effect of the spent grains products used.

Test b: Nicotinic Ester Test

The test was carried out as follows:

Initially, the clear fields were measured with a radiation thermometer and with a laser doppler flowmeter. The test products were then applied.

After 2 hours, the previously treated fields and the clear field were measured again. Thereafter, each measured field, including the clear field, was treated with 0.2 ml of a nicotinic ester product (®Rubriment oil, based on benzyl nicotinate, from Nordmark, Uetersen). Then, after a further 30, 45, 60, 75, 90, 105 and 120 minutes the temperature and microcirculation were measured again. The number of subjects for this test was 20.

It emerged that the spent grains compositions had no measurable effect on the reactions to nicotinic ester in any of the subjects. Accordingly, the spent grains compositions have no vasoconstrictor effect on a nicotinic ester erythema.

Test C: Test of the Antipruritic and Antiinflammatory Effect

O/W(oil in water) and W/0(water in oil) emulsions with the addition of 1 to 5% of spent grains oil were applied to 100 patients, 74 males and 26 females, with a mean age of 32.5 years. The ointments were applied twice a day for 1 to 4 weeks. All the patients tolerated the employed bases well. On comparison of the effects, application of base and base plus spent grains extract on opposite sides, additional antiinflammatory and antipruritic effects were observed in 80% of these subjects after application of the spent grains composition. Thus, the therapeutic effect had its onset after only a few days of application and was increased by further applications.

Test D: Balneotherapeutic Test

Spent grains extracts were used in more than 2,000 bath applications in a total of 230 patients. The concentration of the spent grains extracts in the bath water was 10 ml of extract per 80 l of bath. 50 of the patients suffered from psoriasis vulgaris, 150 from atopic dermatitis, 10 from uremic pruritus, 10 from prurigo and 10 from eczema craquelpe,acu/e/ or preeczematous states. Virtually all the patients reported an emollient effect of the bath, and the skin-care efficacy was assessed as "good". The patients with pruritic dermatoses reported pruritus alleviation of the which persisted for several hours after the bath.

Test E: Test of the Antimycotic Effect

The antimycotic effect of spent grains extract was investigated and compared in one in vitro and one in vivo test. In the therapy model of guinea pig trichophytosis (pathogen: Trichophyton mentagrophytes) the antimycotic effect achieved after 5 treatments with spent grains extract was identical to that with ®Batrafen cream composition (based on ciclopiroxolamine, from Cassella-Riedel, Frankfurt/Main) (see Table 1).

| Product | Diameter of mycosis x in mm | x | Score |
|---|---|---|---|
| Infection control | 10, 11, 16 | 12.3 | |
| Spent grains extract | 7, 8, 7 | 7.3 | 50 |
| Batrafen | 3, 8, 11 | 7.3 | 50 |

II. THERAPEUTIC EFFICACY IN A COMPARATIVE TEST

Spent grains extract baths were applied to a large number of patients who suffered from atopic dermatitis, psoriasis, preeczematous states, pruritus or sebostasis and who had previous experience with the application of commercially available oil baths, for example ®Balneum Hermal (based on soybean oil, from Hermal, Reinbek), ®Oleobal (based on soybean oil, from Heilit, Reinbek), etc. Almost all the patients found the spent grains extract bath to be very pleasant. Many patients reported an emollient effect, with which they were already familiar from oil baths used previously. Patients with pruritic dermatoses, especially patients with atopic dermatitis (patients with a sensitive skin), reported alleviation of the pruritus after application of the bath. Because of this satisfactory experience with the spent grains bath, especially with regard to the antipruritic effect, many patients preferred a spent grains bath to the oil bath previously used.

The examples which follow serve to illustrate the invention further (all quantitative data in percent by weight).

III. MEDICINAL COMPOSITIONS

1. Treatment Cream

| | |
|---|---|
| $CO_2$-extract of spent grains | 10% |
| Propylene glycol monodistearate | 15% |
| Preservative | 0.01% |
| Water ad | 100% |

2. Gel

| | |
|---|---|
| $CO_2$-extract of spent grains | 15% |
| Carboxyvinyl polymers | 2% |
| Preservative | 0.01% |
| Water ad | 100% |

3. Ointment

| | |
|---|---|
| $CO_2$-extract of spent grains | 20% |
| Vegetable oil | 10% |
| Acetyllanolin | 10% |
| Lanolin alcohol | 12% |
| Sorbitan sesquioleate | 2% |
| Water ad | 100% |

4. Alcoholic Lotion

| | |
|---|---|
| $CO_2$-extract of spent grains | 25% |
| Oleyl alcohol | 5% |
| Triethanolamine | 0.5% |
| Alcohol (95%) ad | 100% |

5. Additive for a Medicinal Bath

| | |
|---|---|
| $CO_2$-extract of spent grains | 40% |
| Ammonium lauryl sulfate | 10% |
| Lauryl alcohol | 15% |
| Vegetable oil | 15% |
| Lanolin wax | 5% |
| Diisopropyl adipate | 15% |

IV. COSMETIC COMPOSITIONS

1. W/O Emulsion With $CO_2$-Extract of Spent Grains

| | |
|---|---|
| Glyceryl sorbitan isostearate | 8.0% |
| Methyl glucose dioleate | 2.0% |
| Tallow glycerides | 2.0% |
| Lanolin alcohol | 2.0% |
| Liquid paraffin | 8.0% |
| Isopropyl stearate | 8.0% |
| Silicone oil | 2.0% |
| Vegetable oils | 3.0% |
| Preservative | 0.5% |
| Glycerol | 5.0% |
| Spent grains extract | 5.0% |
| Perfume oil | 0.5% |
| Water ad | 100.0% |

2. Cream Bath With $CO_2$-Extract of Spent Grains

| | |
|---|---|
| Lanolin wax | 5.0% |
| Diisopropyl adipate | 13.0% |
| Liquid paraffin | 5.0% |
| Vegetable oil | 15.0% |
| Spent grains extract | 5.0% |
| Caprylic/caproic glycerides | 5.0% |
| Linolenic acid diethanolamide | 5.0% |
| Perfume oil | 2.0% |
| Lauryl alcohol | 15.0% |
| Lauryl ether sulfate | 30.0% |

3. O/W Emulsion With $CO_2$-Extract of Spent Grains

| | |
|---|---|
| Glycerol monostearate, self-emuls. | 3.0% |

-continued

| | |
|---|---|
| Sorbitan stearate | 2.0% |
| Cetyl alcohol | 3.0% |
| Lanolin alcohol | 5.0% |
| Spent grains extract | 3.0% |
| Isopropyl stearate | 3.0% |
| Vegetable oils | 7.0% |
| Silicone oils | 5.0% |
| Sorbitol | 5.0% |
| Polyacrylic acid | 0.2% |
| Triethanolamine | 0.3% |
| Preservative | 0.4% |
| Water ad | 100.0% |

4. Massage Oil With $CO_2$-Extract of Spent Grains

| | |
|---|---|
| Light liquid paraffin | 48.3% |
| Octyl palmitate | 10.0% |
| Isopropyl stearate | 13.0% |
| Silicone oils | 5.0% |
| Lanolin alcohol | 5.0% |
| Oleyl alcohol | 5.0% |
| VegeTABLE oils | 10.0% |
| Spent grains extract | 3.0% |
| Preservative | 0.2% |
| Perfume oil | 0.5% |

5. Shower Gel With $CO_2$-Extract of Spent Grains

| | |
|---|---|
| Magnesium lauryl ether sulfate | 30.0% |
| Sodium myristyl ether sulfate | 10.0% |
| Lauryl ether sulfate | 15.0% |
| Coconut fatty acid/protein condensate | 5.0% |
| Hydrogenated castor oil | 2.0% |
| Spent grains extract | 3.0% |
| Perfume oil | 1.0% |
| Preservative | 0.5% |
| Water ad | 100.0% |

6. Skin-Care Spray With $CO_2$-Extract of Spent Grains

| | |
|---|---|
| Silicone oils | 0.0% |
| Hydrogenated castor oil | 2.0% |
| Spent grains extract | 3.0% |
| Ethyl alcohol | 82.0% |
| Vitamin F ethyl ester | 2.0% |
| Menthol | 0.5% |
| Perfume oil | 0.5% |
| Can contents: | |
| Active substance | 83 g |
| (R)Frigen 12 ($CCl_2F_2$, from Hoechst AG, Frankfurt/Main) | 43 g |
| (R)Frigen 114 ($CClF_2CClF_2$, from Hoechst AG, Frankfurt/Main) | 28 g |

We claim:

1. Spent brewers' grains extract obtained by extraction of spent brewers' grains with liquid or above-critical $CO_2$ or $N_2O$.

2. A medicinal composition for topical use in the treatment of skin diseases comprising a therapeutically effective amount of spent brewers' grains extract which has been extracted using liquid or above-critical $CO_2$ or $N_2O$, with an acceptable carrier.

3. A medicinal composition of claim 2, wherein the amount of spent brewers' grains extract ranges from about 0.5 to 99% by weight.

4. A medicinal composition of claim 2, wherein the amount of the spent brewers' grains extract ranges from about 5 to 99% by weight.

5. A method of treating a patient suffering from a skin disease which comprises topically administering an effective amount of the medicinal composition of claim 2 to said patient.

6. A method of claim 5, wherein the skin disease is selected from the group consisting of atopic dermatitis, ichthyosis, pruritus, sebostasis, mycoses of the skin and skin irritation caused by jellyfish stings.

7. A method of claim 5, wherein the medicinal composition is administered in the form of a solution, a suspension, an emulsion, a paste, an ointment, a gel, a cream, a lotion, a dusting powder, a soap, a surfactant-containing cleansing product, an oil or a spray.

8. A cosmetic composition for topical use comprising an effective amount of spent brewers' grain extract which has been extracted using liquid or above-critical $CO_2$ or $N_2O$ for treatment of dry skin, dry and irritated skin, irritated skin or a dry scalp with dandruff, with an acceptable carrier.

9. The cosmetic composition of claim 8, wherein the amount of the spent brewers' grains extract ranges from about 0.1 to 99% by weight.

10. A cosmetic composition of claim 8, wherein the amount of spent brewers' grains extract ranges from about 1 to 10% by weight.

11. A method of treating a patient suffering from dry skin, dry and irritated skin, irritated skin or a dry scalp with dandruff, which comprises topically administering an effective amount of the cosmetic composition of claim 8 to said patient.

* * * * *